United States Patent [19]

Fukushima et al.

[11] Patent Number: 4,624,927
[45] Date of Patent: Nov. 25, 1986

[54] REAGENT FOR DETERMINATION OF BLOOD COAGULATION FACTOR XIII

[75] Inventors: Tsunekazu Fukushima; Mitsugu Fujii; Satoshi Funakoshi; Tadakazu Suyama, all of Osaka, Japan

[73] Assignee: The Green Cross Corporation, Osaka, Japan

[21] Appl. No.: 600,740

[22] Filed: Apr. 16, 1984

[30] Foreign Application Priority Data

Apr. 15, 1983 [JP] Japan .................................. 58-66609

[51] Int. Cl.$^4$ .................... G01N 31/00; G01N 33/556
[52] U.S. Cl. ...................................... 436/16; 436/808; 436/521; 436/520
[58] Field of Search ................. 424/12; 436/518-521, 436/808, 8-16, 547; 435/7, 13; 422/61; 23/230 B

[56] References Cited

U.S. PATENT DOCUMENTS

| | | | |
|---|---|---|---|
| 3,925,541 | 12/1975 | Hirata | 436/521 |
| 3,956,477 | 5/1976 | Price et al. | 436/520 |
| 3,987,159 | 10/1976 | Spona et al. | 436/521 |
| 4,136,161 | 1/1979 | Falkowski et al. | 436/521 |
| 4,202,872 | 5/1980 | Collen | 436/520 |
| 4,420,461 | 12/1983 | Reckel et al. | 436/520 |
| 4,426,357 | 1/1984 | Buffington et al. | 436/520 |

Primary Examiner—John F. Terapane
Assistant Examiner—T. J. Wallen
Attorney, Agent, or Firm—Sughrue, Mion, Zinn, Macpeak, and Seas

[57] ABSTRACT

A reagent for determination of human blood coagulation factor XIII for reversed passive hemagglutination reaction which comprises sensitized erythrocytes prepared by sensitizing animal erythrocytes with specific anti-human factor XIII antibody, and a kit using the reagent are disclosed.

6 Claims, No Drawings

REAGENT FOR DETERMINATION OF BLOOD COAGULATION FACTOR XIII

FIELD OF THE INVENTION

This invention relates to a reagent for determination of blood coagulation factor XIII.

BACKGROUND OF THE INVENTION

Human blood coagulation factor XIII (hereinafter referred to briefly as factor XIII) is involved in the formation of a stable fibrin polymer in the final phase of the mechanism of blood coagulation. Known, also, as fibrin stabilizing factor, factor XIII is normally present in an inactive form in the blood but when a coagulation of blood following a bleeding or the like induces the formation of thrombin, it is activated under the influence of this thrombin and calcium ions to stabilize the fibrin. Therefore, in factor XIII-deficient blood, the coagulation time shows a value within the normal range but the fibrin clot formed is so fragile as to induce some characteristic phenomena such as after-bleeding. Therefore, the blood concentration of factor XIII gathered attention as a possible indicator of factor XIII-deficient patients. Today, reagent kits for neutralizing antibody assay and monochloroacetic acid dissolution assay are commercially available.

However, this immunoassay technique for factor XIII determination is so low in detection sensitivity, i.e. a dilution limit only down to 1 to 3% of the factor XIII concentration of healthy humans, that in laboratory tests, for instance the calibration of the factor XIII preparation or the screening test for factor XIII-deficient patients cannot be performed with adequate accuracy. It is, therefore, a problem awaiting a solution to establish an assay method which permits a rapid and accurate determination of factor XIII in a large number of samples.

DETAILED DESCRIPTION OF THE INVENTION

The object of this invention is to provide a reagent for factor XIII determination which has solved the above-mentioned problem.

This invention relates to a factor XIII assay reagent for reversed passive hemagglutination reaction which contains anti-human factor XIII antibody-sensitized erythrocytes prepared by sensitizing animal erythrocytes with specific anti-human factor XIII antibody.

Since the assay reagent according to this invention is more conveniently provided in a kit of component reagents, the following detailed description will refer to this invention as embodied in the form of a kit.

Such a kit according to this invention consists of the following reagents:

(a) anti-human factor XIII antibody-sensitized erythrocytes (briefly, sensitized erythrocytes) obtained by sensitizing animal erythrocytes with anti-human factor XIII antibody;

(b) an assay buffer solution;

(c) a standard human plasma positive control (briefly, positive control); and (d) a standard human plasma negative control (briefly, negative control).

The sensitized erythrocytes are, for the most part, sensitized erythrocytes derived by sensitization of animal erythrocytes with specific anti-human factor XIII antibody. The specific anti-human factor XIII antibody is prepared by immunizing an animal with a high-purity immunization grade of factor XIII (refer to Reference Example) and purifying the antibody from the resulting antiserum. Preparation of this antiserum can be carried out in the known manner. For example, a mixed emulsion of high-purity human factor XIII and Freund's complete adjuvant is prapared and intradermally injected into an animal from 5 to 6 times. After a few weeks, the blood is collected and allowed to coagulate at room temperature. The coagulated blood is allowed to stand at 4° C. overnight and, then, centrifuged at 3000 rpm for 20 minutes to give the aforesaid antiserum. Since the capacity of producing antibodies to human factor XIII varies with different animal species, it is economically advantageous to select highly sensitive animals such as the guinea pig, rabbit, domestic fowl, horse, etc.

The purification of the anti-serum for recovery of the antibody for sensitization can be carried out, for example in the following manner. First, a concentrate of factor XIII is mixed with the antiserum (rabbit) to prepare an antigen-antibody complex. This complex is washed thoroughly with physiological saline to remove other serum components and excess antigen and antibody, and the washed complex is dissolved by the addition of urea (or guanidine hydrochloride), whereby the antigen factor XIII is inactivated ad solubilized. The urea is fractionally removed by gel filtration chromatography or the like, after which the complex is subjected to affinity chromatograpy on an anti-rabbit IgG-containing stationary phase using a solution of guanidine hydrochloride, urea, potassium thiocyanate or the like as the eluent, whereby a high-purity anti-factor XIII antibody for sensitization is obtained.

The erythrocytes to be sensitized with the anti-human factor XIII antibody may be obtained from virtually any species of animal. However, in order to prepare a stable and highly sensitive reagent, sheep erythrocytes, domestic fowl erythrocytes or group O human erythrocytes preferable. The erythrocytes are washed well with physiological saline and stabilized by treatment with glutaraldehyde, formalin or the like.

The erythrocytes are preferably within the range of about 5 to 15 $\mu$m. The sensitization of these erythrocytes with said purified antibody can be conducted in the known manner [refer to Advances in Medicine 78, 759 (1970)]. Thus, the sensitization of erythrocytes with the antibody is preferably carried out in a buffer solution, and generally, a suspension of the erythrocytes is mixed with a liquid containing the antibody.

This procedure is preferably performed at pH 5.0 to 8.5 and at a temperature of 20° to 60° C. The erythrocytes thus sensitized are lyophilized and kept in a vial, for instance, preferably with the inclusion of a preservative agent such as sodium azide.

The positive control included in the kit according to this invention is used for the construction of a standard calibration curve, and is generally a lyophilisate containing human factor XIII.

The human factor XIII is dissolved in a buffer solution, and the stock solution so prepared is diluted in 4 to 6 concentration levels within the range of, for example, 5 ng/ml to 50 ng/ml for use in the construction of the standard calibration curve.

The positive control is kept in a vial, for instance, preferably with the addition of a preservative such as sodium azide.

The negative control is a liquid for which both the human anti-factor XIII antibody and the human factor XIII are negative (for example, human serum, physiological saline, etc.), and is kept in a vial, for instance, preferably with the addition of a preservative such as sodium azide.

The assay buffer is a buffer solution used for diluting the sensitized erythrocytes, positive control and negative control, and may for example be a phosphate buffer solution. To prevent occurence of non-specific reactions, the buffer may be supplemented with, for example, stroma, animal serum or the like. It is also preferable to add a preservative such as sodium azide to the assay buffer.

The following examples, test example and reference example are intended to illustrate this invention in further detail.

The activity of factor XIII was calculated with the titer of the factor XIII activity in 1 ml of fresh healthy human plasma being taken as unity [The dilution assay procedure is described in Thrombosis et Diathesis Haemorrhagica 23, 455 (1970)]

EXAMPLE 1

A rabbit was immunized with 2 mg (as protein) of purified human XIII to give an anti-human factor XIII serum. A 3 ml portion of this antiserum was mixed with 8 units of purified factor XIII and the mixture was incubated at 37° C. for 2 hours. The mixture was then centrifuged, and the supernatant discarded, and the sedimented antigen-antibody complex was thoroughly washed with cold physiological saline at 4° C. The washed sediment was dissolved by the addition of a small quantity of urea and desalted by Sephadex G-25 column chromatography and further subjected to affinity chromatography on an anti-rabbit IgG(swine)-Sepharose column using 5M guanidine hydrochloride as the eluent. The eluate was dialyzed against a phosphate buffer solution (pH 7.2) to give 3.3 mg of purified antibody for sensitization. To prepare animal erythrocytes to be sensitized, sheep erythrocytes were washed well with phosphate buffer, and glutaraldehyde was added to give a final concentration of 0.5% w/v. The mixture was allowed to stand at room temperature for about 1 hour, after which it was washed with the same phosphate buffer as above to remove the glutaraldehyde, whereby stabilized erythrocytes were obtained.

A 5% w/v suspension of the stabilized erythrocytes was mixed with an equal volume of the above purified human factor XIII antibody (about 0.01 at E 280 nm), followed by addition of 5 to 300 mg/dl of tannic acid at pH 7.2 and stirring. The mixture was allowed to stand at 4° C. overnight to give anti-human factor XIII antibody-sensitized erythrocytes. The erythrocytes were washed thoroughly with the same phosphate buffer, distributed into vials and lyophilized to give a reagent.

The lyophilized anti-human factor XIII antibody-sensitized erythrocytes were dissolved to a concentration of 0.5% in phosphate buffer solution prepared by adding at 2% of sheep erythrocyte stroma to an isotonic phosphate buffer (pH 7.2) containing an animal serum and sodium chloride, and the hemagglutigation reaction to human factor XIII was determined by the microplate method. This system permitted a determination up to 1 to 2 ng/ml of human factor XIII in the sample.

EXAMPLE 2

The following five component reagents are included in the kit according to this invention.

(1) Anti-human factor XIII antibody-sensitized sheep erythrocytes:

Each vial contains lyophylized sensitized sheep erythrocytes and a preservative, and when the contents of the vial are suspended by the addition of 5 ml of phosphate buffer solution (PBS, see (5) below), a 0.5% (w/v) erythrocyte suspension is obtained. As said preservative, 1 mg of sodium azide is contained.

(2) Human factor XIII positive control:

Each vial contains 1 ml of sterile-filtered human factor XIII. The concentration of human factor XIII in this solution as assayed by the RPHA method is not less than 1:64. As a preservative, 1 mg (0.1%) of sodium azide is contained.

(3) Human factor XIII negative control:

Each vial contains 1 ml of sterile-filtered human serum which is negative for both anti-human factor XIII antibody and human factor XIII antigen or 1 ml of physiological saline. As a preservative, 1 mg (0.1%) of sodium azide is contained.

(4) Phosphate buffer:

Each vial contains 50 ml of a sterile-filtered isotonic sodium chloride-containing phosphate buffer solution (PBS, pH 7.2). To prevent non-specific reaction in the assay, solubilized stroma and animal serum have been added to the PBS.

| Composition of PBS (in 50 ml) | |
| --- | --- |
| Disodium phosphate (anhydrous) | 395 mg |
| Monopotassium phosphate | 155 mg |
| Sodium chloride | 255 mg |
| Stroma | 3% |
| Animal serum | 1% |
| Sodium azide | 50 mg |
| | pH 7.2 |

A 10 ml portion of the phosphate buffer is used for suspending the anti-human factor XIII antibody-sensitized sheep erythrocytes, and the remainder is used in the dilution of test samples. Preferably, 1 mg (0.1%) of sodium azide is added as a preservative.

(5) A reagent for verification of specificity:

Each vial contains a lyophilisate of sterile-filtered purified anti-human factor XIII antibody (PHA value: $\geq 1:512$). The lyophilisate is dissolved in 5 ml of physiological saline.

EXAMPLE 3

An assay trial using the reagent kit of Example 2.

(1) The anti-human factor XIII antibody-sensitized sheep erythrocytes are suspended in phosphate buffer (5 ml per vial of erythrocytes).

(2) Using a dropper, the phosphate buffer is put in 25 μl portions into the wells of a U-plate.

(3) Using a dropper, the sample is put in 25 μl portions into the wells in A row. Using a diluter, the mixture in the wells in A row is transferred to the wells in B row, and then the mixture in B row is transferred to the wells in C row. The procedure is serially repeated to finally transfer the fluid to the wells in J row. In the above procedure, the sample is diluted two-fold each transfer stage so that the dilution in J row is a 1024-fold dilution.

(4) The same procedure as (3) is followed for the positive control and the negative control to prepare the respective dilution series.

(5) Using a dropper, a suspension of anti-human factor XIII antibody-sensitized sheep erythrocytes in phosphate buffer is added in 25 μl portions to all the wells.

(6) The U plate is shaken on a micromixer for about 10 seconds and, then, incubated at room temperature for 2 hours.

(7) Observation of controls:

As to the positive controls, hemagglutination is usually found at a dilution factor of 64-fold or more. As for the negative control, sediments of erythrocytes are found on the bottoms of all wells from A row through J row. (When a determination is satisfactory, the negative image is small and well-defined.

(8) Results of assay:

The result for the sample is compared with the result for the negative control and the highest dilution factor giving rise to hemagglutination is taken as human factor XIII.

EXPERIMENTAL EXAMPLE

When the following samples were tested using the RPHA factor XIII assay reagent obtained in Example 1, factor XIII could be detected with high sensitivity.

In the standard dilution series prepared using the standard human plasma and factor XIII (1 unit/ml), determination down to the level of 0.01% (0.001 unit/ml) (1/10000 in healthy humans) is possible.

The nonspecific agglutination value determined using the fresh plasma of healthy humans (29 volunteers) was X16 to X32. In any of the determinations, no prozone effect was noted.

REFERENCE EXAMPLE

An aqueous solution of purified factor XIII (403 units/ml) obtained by the method of Japanese Patent Kokai Sho 55-64522 from 800 l of a physiological saline extract of human placentas (about 840 placentas, ca. 510 kg) was adjusted to pH 7.0 and 10° C., and, then, fractionated with the addition of 80 g/l of sodium sulfate. The precipitate was recovered and dissolved in water, and the solution was dialyzed against a 0.5% aqueous solution of sodium chloride supplemented with 2.25% of glycine. The dialysate was sterile-filtered, distributed into vials and lyophilized. Assuming that the amount of factor XIII activity in 1 ml of fresh healthy human plasma is 1 unit, the factor XIII obtained had an activity of 4,500 thousand units, and was 75 g as protein.

What is claimed is:

1. A reagent for determination of human blood coagulation factor XIII for reversed passive hemagglutination reaction which comprises sensitized erythrocytes prepared by sensitizing animal erythrocytes with specific anti-human factor XIII antibody.

2. A kit for determination of human blood coagulation factor XIII for reversed passive hemagglutination reaction which comprises:
   (a) sensitized erythrocytes prepared by sensitizing animal erythrocytes with specific anti-human factor XIII antibody;
   (b) an assay buffer solution;
   (c) a standard human plasma positive control; and
   (d) a standard human plasma negative control.

3. A reagent for determination of human blood coagulation factor XIII for reversed phase hemagglutination reaction as claimed in claim 1 or 2 wherein said animal erythrocytes are selected from the group consisting of sheep erythrocytes, domestic fowl erythrocytes and group O human erythrocytes.

4. A kit for determination of human blood coagulation factor XIII for reversed passive hemagglutination reaction as claimed in claim 2, which further includes a reagent for verification of the specificity of hemagglutination reaction, said reagent for verification being a lyophilisate of sterile-filtered anti-human factor XIII antibody.

5. A kit for determination of human blood coagulation factor XIII for reversed phase hemagglutination reaction as claimed in claim 2, wherein each of said components (a), (b), (c) and (d) contains a stabilizing amount of a preservative.

6. A kit for determination of human blood coagulation factor XIII for reversed phase hemagglutination reaction as claimed in claim 5 wherein said preservative is sodium azide.

* * * * *